US012740753B2

United States Patent

(12) United States Patent
Miyashita et al.

(10) Patent No.: US 12,740,753 B2
(45) Date of Patent: Sep. 22, 2026

(54) RADIATION IMAGING APPARATUS, RADIATION IMAGING SYSTEM, AND MANUFACTURING METHOD FOR RADIATION IMAGING APPARATUS

(71) Applicant: CANON KABUSHIKI KAISHA, Tokyo (JP)

(72) Inventors: Kaito Miyashita, Kanagawa (JP); Takaaki Gonda, Kanagawa (JP); Tomohiro Hoshina, Kanagawa (JP); Akira Kida, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 155 days.

(21) Appl. No.: 18/740,285

(22) Filed: Jun. 11, 2024

(65) Prior Publication Data

US 2024/0418875 A1 Dec. 19, 2024

(30) Foreign Application Priority Data

Jun. 13, 2023 (JP) ................................ 2023-097243

(51) Int. Cl.

*A61B 6/42* (2024.01)
*G01T 1/20* (2006.01)
*G01T 1/24* (2006.01)

(52) U.S. Cl.

CPC ........ *A61B 6/4233* (2013.01); *G01T 1/20189* (2020.05); *G01T 1/244* (2013.01)

(58) Field of Classification Search

None

See application file for complete search history.

(56) References Cited

U.S. PATENT DOCUMENTS 6,025,598 A * 2/2000 Tago ........................ G01T 1/244 250/370.08
9,529,094 B2 * 12/2016 Ishii ...................... G01T 1/1642
10,283,555 B2 * 5/2019 Ichimura ............. H10F 39/1898
11,269,087 B2 * 3/2022 Hoshina ................... A61B 6/00
12,379,510 B2 * 8/2025 Ide ............................ G01T 1/24

(Continued)

FOREIGN PATENT DOCUMENTS

JP 2015052535 A 3/2015
JP 2019141256 A * 8/2019 ............ H02J 7/0044
WO WO-2011152323 A1 * 12/2011 ........... G01T 1/2006

*Primary Examiner* — Thomas R Artman

(74) *Attorney, Agent, or Firm* — Canon U.S.A., Inc. IP Division

(57) ABSTRACT

A radiation imaging apparatus including a sensor panel including a first surface provided with a pixel array and an electrical connector and a second surface, and a base configured to support the second surface through first and second members, is provided. In an orthogonal projection to the first surface, the electrical connector is provided between a region provided with the first member provided to overlap the pixel array and an outer edge of the panel and the second member is provided to overlap the electrical connector. The second member is fixed to at least one of the second surface, the base, and the first member, and a passage extending from the first member to the outer edge is provided between the second surface and the base not to overlap the second member in an orthogonal projection to the first surface.

12 Claims, 9 Drawing Sheets

(56) References Cited

U.S. PATENT DOCUMENTS

| | | | | |
|---|---|---|---|---|
| 2016/0070002 | A1* | 3/2016 | Ishii | G01T 1/20<br>250/361 R |
| 2016/0181308 | A1* | 6/2016 | Ichimura | H10F 39/1898<br>257/428 |
| 2020/0379130 | A1* | 12/2020 | Hoshina | G01T 1/2006 |
| 2023/0375728 | A1* | 11/2023 | Ide | A61B 6/4208 |
| 2024/0418875 | A1* | 12/2024 | Miyashita | G01T 1/20184 |

* cited by examiner

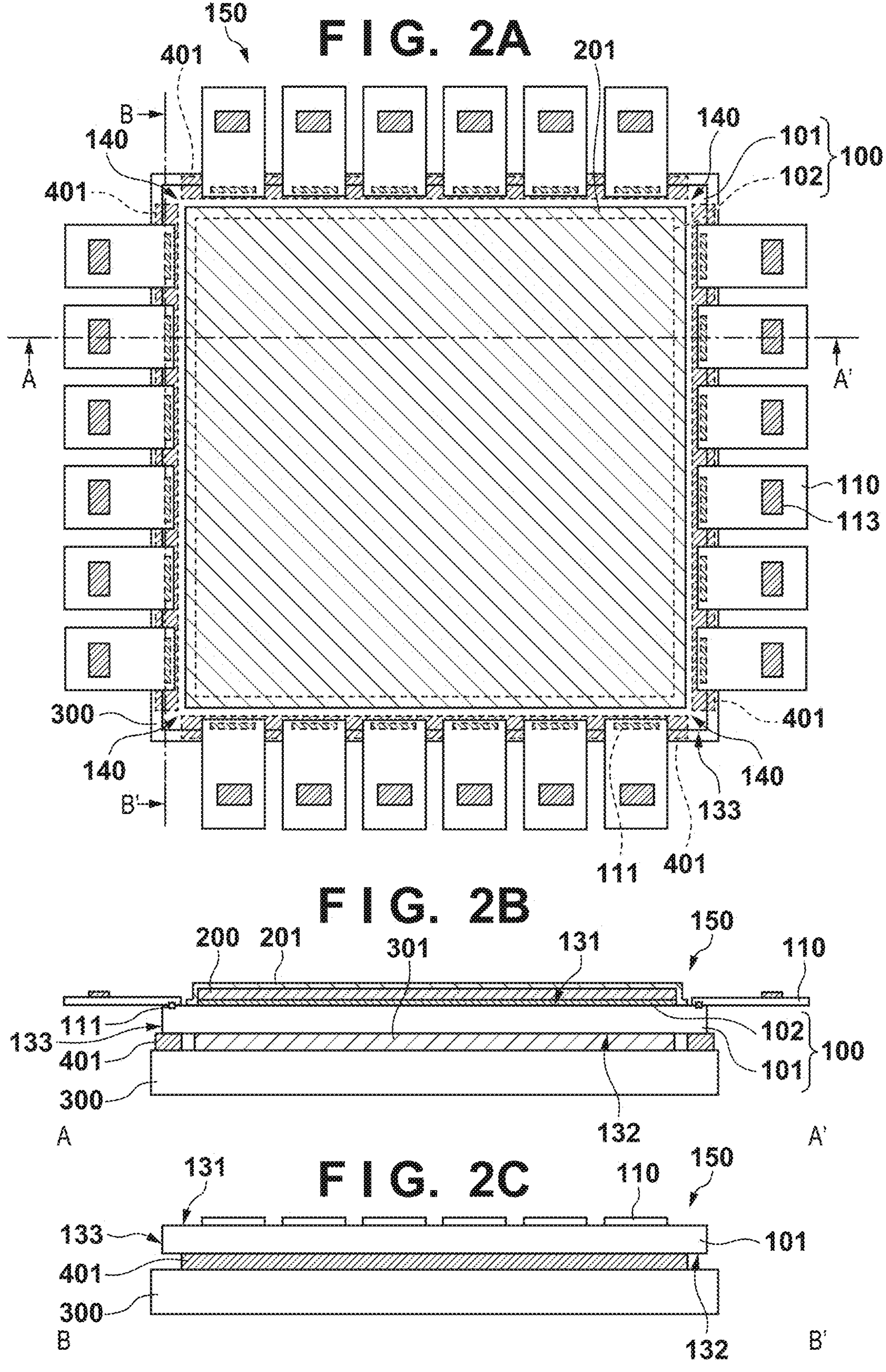
F I G. 2A
150
401
201
B
140
101
100
102
401
A
A'
110
113
300
401
140
140
133
B'
111
401
F I G. 2B
200
201
301
131
150
110
111
133
401
300
102
101
132
A
A'
F I G. 2C
131
110
150
133
101
401
300
B
132
B'

F I G. 7A
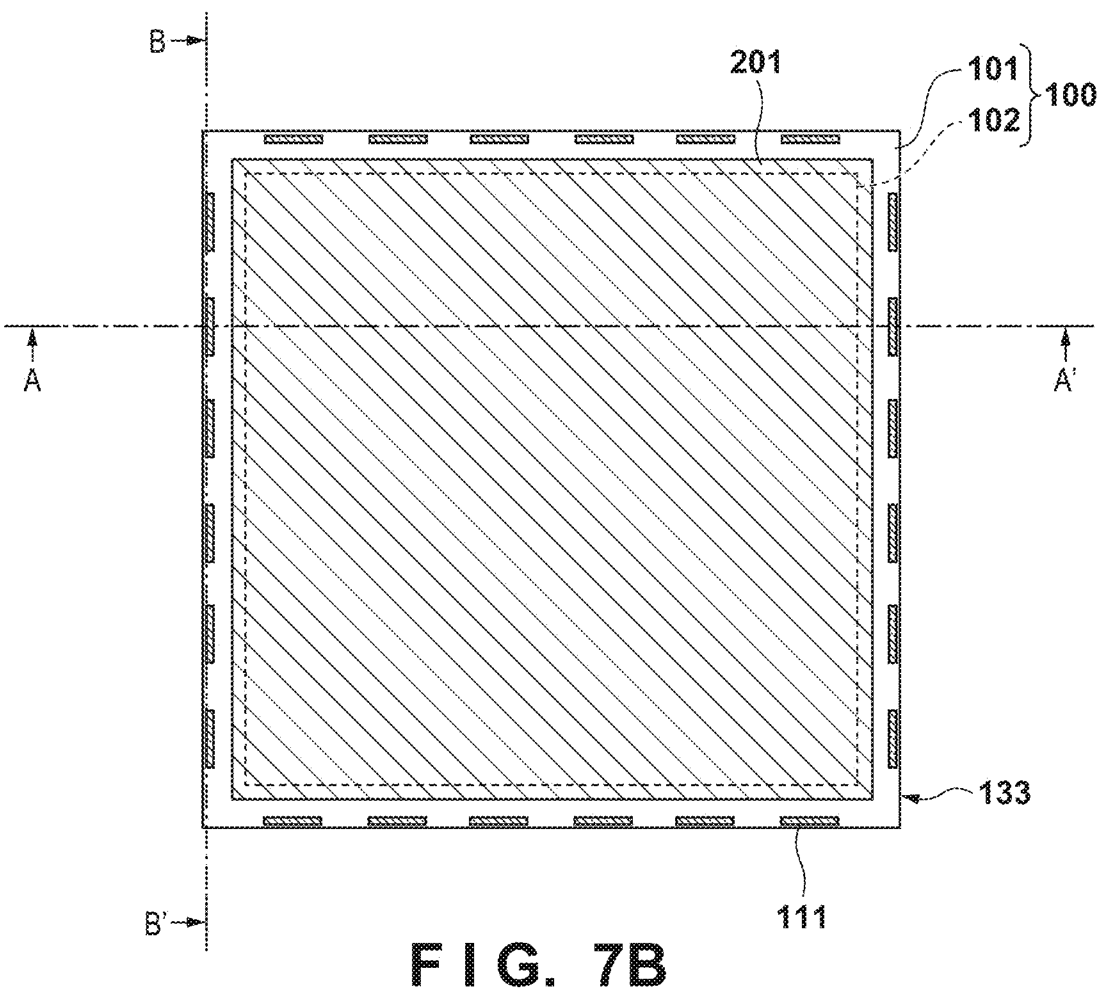
F I G. 7B
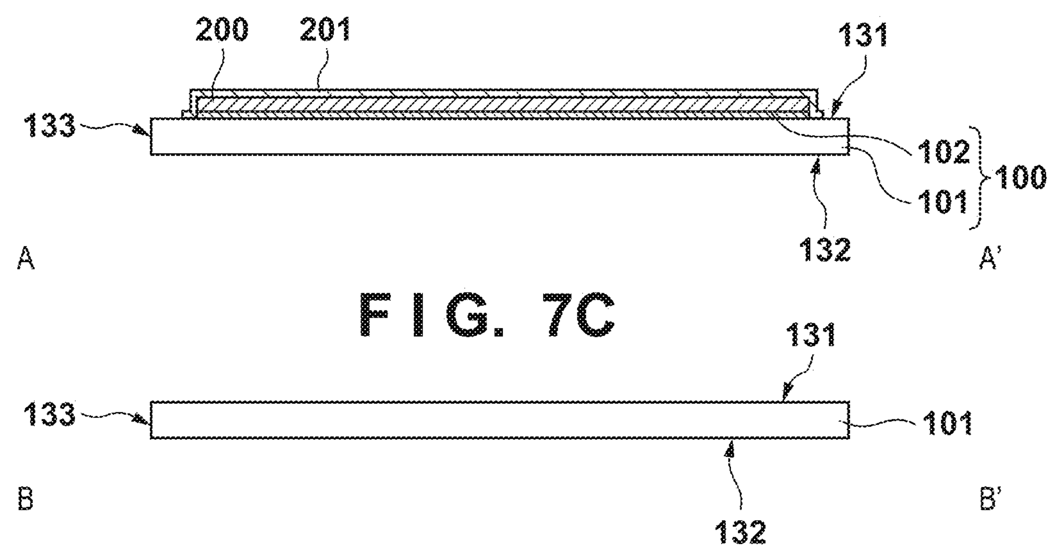
F I G. 7C 600
112
201
200
110
111
102
100
101
600

201
101
100
102
R
110
113
300
133
111

110
200
201
301
131
R
111
133
102
100
101
300
132
401
A
A'

RADIATION IMAGING APPARATUS, RADIATION IMAGING SYSTEM, AND MANUFACTURING METHOD FOR RADIATION IMAGING APPARATUS

BACKGROUND

Field

The present disclosure relates to a radiation imaging apparatus, a radiation imaging system, and a manufacturing method for the radiation imaging apparatus.

Description of the Related Art

Japanese Patent Laid-Open No. 2015-052535 discloses a radiation detection apparatus including a sensor panel provided with a pixel array and electrical connection portions to which wiring members for reading out signals from the pixel array to the outside are connected. According to Japanese Patent Laid-Open No. 2015-052535, when wiring members are pressure-bonded to electrical connection portions, breakage and deformation of a sensor panel are suppressed by supporting the electrical connection portions with a frame-like support member.

In the arrangement shown in Japanese Patent Laid-Open No. 2015-052535, when the environmental temperature changes, an atmospheric pressure difference can occur between the space surrounded by the frame-like support member, the sensor panel, and the support substrate and the external space. If the sensor panel is distorted by an atmospheric pressure difference, an artifact can occur in an image obtained by the sensor panel.

SUMMARY

Some embodiments of the present disclosure provide techniques advantageous in suppressing a deterioration in image quality.

According to some embodiments, a radiation imaging apparatus may include: a sensor panel including a first surface provided with a pixel array and an electrical connection portion and a second surface on an opposite side to the first surface; a wiring member connected to the electrical connection portion; and a support base configured to support the second surface through a first support member and a second support member, wherein in an orthogonal projection to the first surface, the electrical connection portion is provided between a region provided with the first support member provided so as to overlap the pixel array and an outer edge of the sensor panel and the second support member is provided so as to overlap the electrical connection portion, the second support member is fixed to at least one of the second surface, the support base, and the first support member, and a passage extending from the first support member to the outer edge is provided between the second surface and the support base so as not to overlap the second support member in an orthogonal projection to the first surface, is provided.

According to some other embodiments, a manufacturing method for a radiation imaging apparatus may include: preparing a sensor panel including a first surface provided with a pixel array and an electrical connection portion and a second surface on an opposite side to the first surface; and fixing the sensor panel to a support base supporting the second surface through a first support member, wherein the electrical connection portion is provided between a region provided with the first support member provided so as to overlap the pixel array and an outer edge of the sensor panel in an orthogonal projection to the first surface, the method can further include providing a second support member between the second surface and the support base so as to overlap the electrical connection portion to support the electrical connection portion, and connecting a wiring member to the electrical connection portion, the second support member is fixed to at least one of the second surface, the support base, and the first support member, and a passage extending from the first support member to the outer edge is provided between the second surface and the support base so as not to overlap the second support member in an orthogonal projection to the first surface, is provided.

Further features of the present disclosure will become apparent from the following description of exemplary embodiments (with reference to the attached drawings).

BRIEF DESCRIPTION OF THE DRAWINGS

FIGS. 2A to 2C are views showing an example of the arrangement of the radiation imaging apparatus according to this embodiment.

FIGS. 6A to 6C are views showing an example of the arrangement of the radiation imaging apparatus according to this embodiment.

FIGS. 7A to 7C are views showing an example of a manufacturing method for the radiation imaging apparatus according to this embodiment.

DESCRIPTION OF THE EMBODIMENTS

Figure 1:
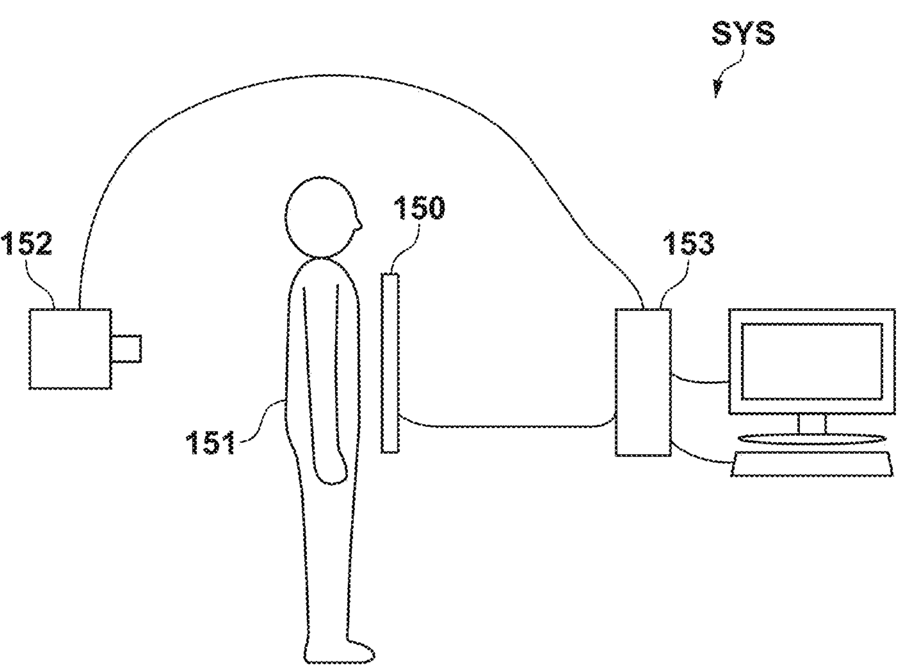
FIG. 1 is a view showing an example of the arrangement of a radiation imaging system including a radiation imaging apparatus according to some embodiments.
Figure 3A:
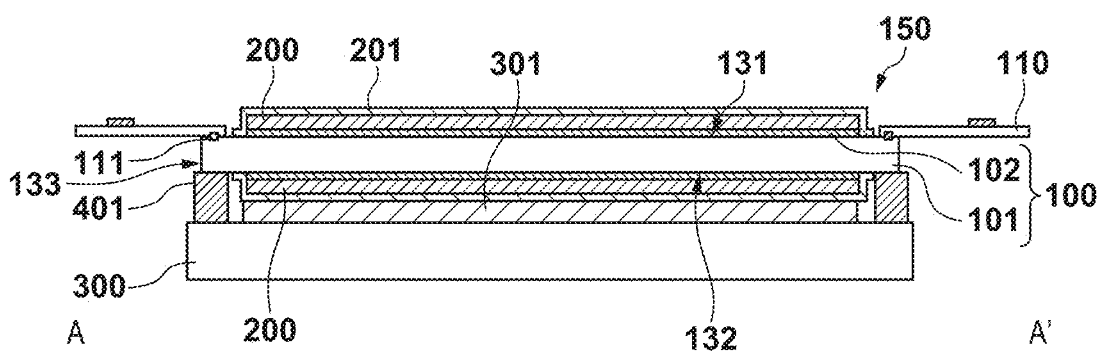
FIGS. 3A and 3B are views showing an example of the arrangement of the radiation imaging apparatus according to this embodiment.
Figure 3B:
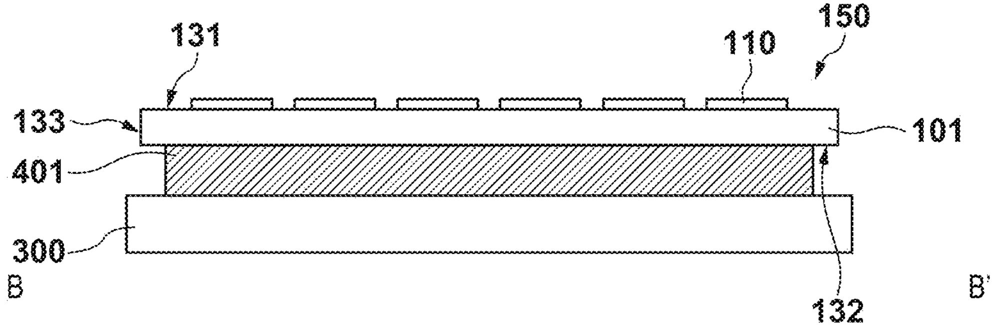

Hereinafter, various exemplary embodiments, features, and aspects will be described in detail with reference to the attached drawings. Note, the following embodiments are not intended to limit the scope of the claimed invention. Multiple features are described in the embodiments, but limitation is not made to the disclosure that uses all such features, and multiple such features may be combined as appropriate. Furthermore, in the attached drawings, the same reference numerals are given to the same or similar configurations, and redundant description thereof is omitted.

Note that radiation according to this disclosure can include not only α-rays, β-rays, and γ-rays that are beams generated by particles (including photons) emitted by radioactive decay but also beams having energy equal to or higher than the energy of these beams, for example, X-rays, particle rays, and cosmic rays.

A radiation imaging apparatus according to an embodiment of this disclosure will be described with reference to FIG. 1 to FIGS. 10A and 10B. FIG. 1 is a schematic view showing an example of the arrangement of a radiation imaging system SYS using a radiation imaging apparatus 150 according to this embodiment. The radiation imaging system SYS can include the radiation imaging apparatus 150, a radiation generating apparatus 152, and a processing apparatus 153. The radiation imaging apparatus 150 and the radiation generating apparatus 152 are connected to the processing apparatus 153. The radiation generating apparatus 152 emits radiation under the control of the processing apparatus 153. The radiation imaging apparatus 150 detects the radiation emitted from the radiation generating apparatus 152 and transmitted through a subject 151. The radiation imaging apparatus 150 transmits the information of the detected radiation as a signal to the processing apparatus 153. The processing apparatus 153 performs desired arithmetic processing. The processing apparatus 153 generates, for example, a radiation image for diagnosis from the information of the radiation detected by the radiation imaging apparatus 150. FIG. 1 shows that wired connection is made between the radiation imaging apparatus 150 and the processing apparatus 153 and between the radiation generating apparatus 152 and the processing apparatus 153. However, this is not exhaustive and wireless connection may be made between them.

FIGS. 2A to 2C are schematic views showing an example of the arrangement of the radiation imaging apparatus 150 according to this embodiment. FIG. 2A is a plan view of the radiation imaging apparatus 150. FIG. 2B is a sectional view taken along A-A' shown in FIG. 2A. FIG. 2C is a sectional view taken along B-B' shown in FIG. 2A.

The radiation imaging apparatus 150 includes a sensor panel 100, wiring members 110, and a support base 300. The sensor panel 100 includes a surface 131 provided with a pixel array 102 and electrical connection portions 111 and a surface 132 on the opposite side to the surface 131. The support base 300 supports the surface 132 of the sensor panel 100 through a support member 301 and a support member 401. The sensor panel 100 includes a substrate 101 made of a semiconductor such as silicon, glass, plastic, or the like. The pixel array 102 is provided on the surface 131 of the sensor panel 100 (the substrate 101). Pixels each including a conversion element that converts radiation or light into an electrical signal and a switch element such as a TFT (thin film transistor) are provided on the pixel array 102 in, for example, a two-dimensional pattern.

For example, amorphous selenium (a-Se) that directly converts radiation into an electrical signal may be used for each conversion element provided on the pixel array 102. Alternatively, as shown in FIG. 2B, for example, a combination of a scintillator 200 and a photosensor (photoelectric conversion element), such as a photodiode or photocapacitor, which converts the light converted from the radiation by the scintillator 200 into an electrical signal may be used for each conversion element provided on the pixel array 102. A photoelectric conversion element can be formed from a semiconductor such as amorphous silicon or oxide semiconductor such as IGZO (indium gallium zinc oxide).

The electrical connection portions 111 are provided on the periphery of the pixel array 102 on the surface 131 of the sensor panel 100. More specifically, the electrical connection portions 111 are provided between the region on which the support member 301 supporting the pixel array 102 is provided and an outer edge 133 of the sensor panel 100 in an orthogonal projection to the surface 131 of the sensor panel 100. The wiring members 110 are connected to the electrical connection portions 111 provided on the surface 131 of the sensor panel 100. Signals and power for operating the pixel array 102 are supplied via the wiring members 110 and the electrical connection portions 111, and signals generated by the pixel array 102 are output from the sensor panel 100 to the outside.

The wiring members 110 are positioned outside the pixel array 102 and are electrically connected to the pixel array 102, as described above. In this embodiment, the plurality of electrical connection portions 111 are provided on the surface 131 of the sensor panel 100, and the plurality of wiring members 110 are provided to respectively correspond to the electrical connection portions 111. As shown in FIG. 2A, the electrical connection portions 111 and the wiring members 110 may be provided on the respective four sides of the rectangular pixel array 102. However, this is not exhaustive, and the electrical connection portions 111 and the wiring members 110 may be provided along only one side, along two adjacent or opposite sides, or along three sides. In addition, the wiring members 110 may be connected to all the electrical connection portions 111 provided on the sensor panel 100. However, some of the electrical connection portions 111 may not be connected to the wiring members 110 in accordance with the design or the like of the sensor panel 100.

In the case shown in FIGS. 2A to 2C, the sensor panel 100 is formed of one sensor chip. However, this is not exhaustive, and the sensor panel 100 may be formed of a plurality of sensor chips. The pixel array 102 may be covered with a protective layer using an inorganic film such as a silicon oxide film or a silicon nitride film. In addition, a passivation film using an organic film such as a polyimide film may be provided on the protective film to flatten the surface of the sensor panel 100.

A flexible board or the like can be used for the wiring member 110. For example, the wiring member 110 is connected to a circuit board (not shown) provided with an electric circuit which is provided on the surface 132 of the sensor panel 100 and serves to operate the pixel array 102. For example, a printed wiring board on which a semiconductor chip including a desired circuit is mounted is used for the circuit board. Circuits 113 for operating the pixel array 102 may be provided on the wiring members 110. The circuit 113 can include, for example, a driving circuit for driving the pixel array 102 and a signal processing circuit for performing signal processing such as amplification of an electrical signal read out from the pixel array 102. The wiring member 110 is joined to the electrical connection portion 111 provided on the surface 131 of the sensor panel 100 with a joining member 112 (shown in FIG. 8) such as an anisotropic conductive film and is electrically connected to the pixel array 102.

In this embodiment, as described above, the scintillator 200 is provided as part of a conversion element. The scintillator 200 can be shared by a plurality of photoelectric conversion elements. The scintillator 200 is provided on the surface 131 of the sensor panel 100 so as to cover the pixel array 102 provided on the surface 131 of the sensor panel 100. However, this is not exhaustive, and the scintillator 200 may also be provided on the surface 132 of the sensor panel 100 as in the arrangement shown in FIGS. 3A and 3B in, for example, the case in which the substrate 101 is transparent. In an orthogonal projection to the surface 131 of the sensor panel 100, the scintillator 200 is provided on the surface 131 (also on the surface 132) of the sensor panel 100 at a position covering the pixel array 102.

The scintillator 200 converts radiation entering the radiation imaging apparatus 150 into light (for example, visible light) having a wavelength that can be detected by the photoelectric conversion elements provided on the pixel array 102. For example, an alkali halide material represented by CsI:TI obtained by doping cesium iodide with thallium (Tl) may be used for the scintillator 200. Alternatively, a powder phosphor (which can also be called GOS) obtained by doping a matrix of a metal oxysulfide (for example, $Gd_2O_2S$) with a small amount of trivalent rare earth such as terbium or europium as a light emission center may be used for the scintillator 200. As described above, when the conversion elements provided on the pixel array 102 directly convert radiation into electrical signals, the scintillator 200 is omitted.

A surface of the scintillator 200 which is not in contact with the sensor panel 100 may be covered with a scintillator protective layer 201. The scintillator protective layer 201 is provided to suppress decreases in light emission amount and sharpness due to moisture absorption by the scintillator 200. The scintillator protective layer 201 can be formed by bonding a resin with low moisture permeability or a sheet with low moisture permeability to a surface of the scintillator 200 through an adhesive layer such as an adhesive agent or adhesive compound. Examples of the resin with low moisture permeability include chlorine-based resins such as polyparaxylene and polyvinylidene chloride and fluorine-based resins such as polychlorotrifluoroethylene and polyvinylidenefluoride. Examples of the sheet with low moisture permeability include metal foils such as aluminum, silver, and copper in addition to resin sheets. In the arrangement shown in FIGS. 2B and 3A, the scintillator protective layer 201 is formed by bonding an aluminum sheet to the scintillator 200 by using an adhesive compound.

The support member 301 is provided so as to overlap the pixel array 102 in an orthogonal projection to the surface 131 of the sensor panel 100. As shown in FIG. 2B, the pixel array 102 may be equal in size to the support member 301. The support member 301 is a member for supporting a region of the substrate 101 which includes at least the pixel array 102 from the surface 132 side of the sensor panel 100. In other words, the support base 300 supports the pixel array 102 from the surface 132 side of the sensor panel 100 through the support member 301. A metal material such as stainless steel, aluminum, or molybdenum, glass, ceramic, or the like can be used for the support base 300. The support member 301 can be a member for joining the support base 300 to the sensor panel 100.

The support member 401 is provided so as to overlap at least one of the electrical connection portions 111 provided on the sensor panel 100. The support member 401 supports the sensor panel 100 from the surface 132 side in a region where no support member 301 is provided. The support member 401 is fixed to at least one of the surface 132 of the sensor panel 100, the support base 300, and the support member 301.

As shown in FIG. 2A, a plurality of support members 401 may be provided. For example, the plurality of support members 401 may be intermittently provided so as to surround the pixel array 102 in an orthogonal projection to the surface 131 of the sensor panel 100. In any case, a passage 140 is provided between the surface 132 of the sensor panel 100 and the support base 300 so as to extend from the support member 301 to the outer edge 133 of the sensor panel 100 without overlapping the support member 301 in an orthogonal projection to the surface 131 of the sensor panel 100. That is, as shown in FIG. 2A, even if the support member 401 is provided so as to surround the pixel array 102, the support member 401 does not continuously surround the pixel array 102.

When the support member 401 continuously surrounds the pixel array 102, a change in environmental temperature can cause an atmospheric pressure difference between the space surrounded by the support member 401, the sensor panel 100, and the support base 300 and the external space. If an atmospheric pressure difference occurs, an artifact may occur in an obtained image due to the distortion of the sensor panel 100 and the like. In addition, when, for example, the support member 401 is fixed to the sensor panel 100 and the support base 300, a change in environmental temperature can cause distortion due to the expansion coefficient difference between the sensor panel 100 and the support base 300. This can cause an artifact. Such mechanical distortion can cause damage and failure of the sensor panel 100.

In this embodiment, the passage 140 extending from the support member 301 to the outer edge 133 of the sensor panel 100 is provided between the surface 132 of the sensor panel 100 and the support base 300 without providing any support member 401. The passage 140 serves to prevent an atmospheric pressure difference between the space surrounded by the support member 401, the sensor panel 100, and the support base 300 and the external space. Even if the support member 401 is fixed to the sensor panel 100 and the support base 300, providing the passage 140 makes it possible to reduce the distortion due to the expansion coefficient difference between the sensor panel 100 and the support base 300 with a change in environmental temperature. This enables the radiation imaging apparatus 150 according to this embodiment to suppress a deterioration in image quality due to, for example, the occurrence of an artifact. It is also possible to suppress damage and failure of the sensor panel 100 provided in the radiation imaging apparatus 150.

The support member 401 may be, for example, a resin that joins the surface 132 of the sensor panel 100 to the support base 300. Alternatively, for example, the support member 401 may be a sheet-like member having an adhesive surface. In addition, the support member 401 may be formed of a plurality of members. For example, the support member 401 may be formed of a plate-like member provided on the support base 300 so as to overlap the electrical connection portions 111 and a joining member using a hardening resin that joins the plate-like member to the surface 132 of the sensor panel 100. In this case, the support member 401 is fixed to the surface 132 of the sensor panel 100 with the joining member. Accordingly, the support member 401 may be fixed to at least one of the support member 301 and the support base 300 or may not be fixed to the support member 301 and the support base 300.

Figures 4A, 4B, 4C:
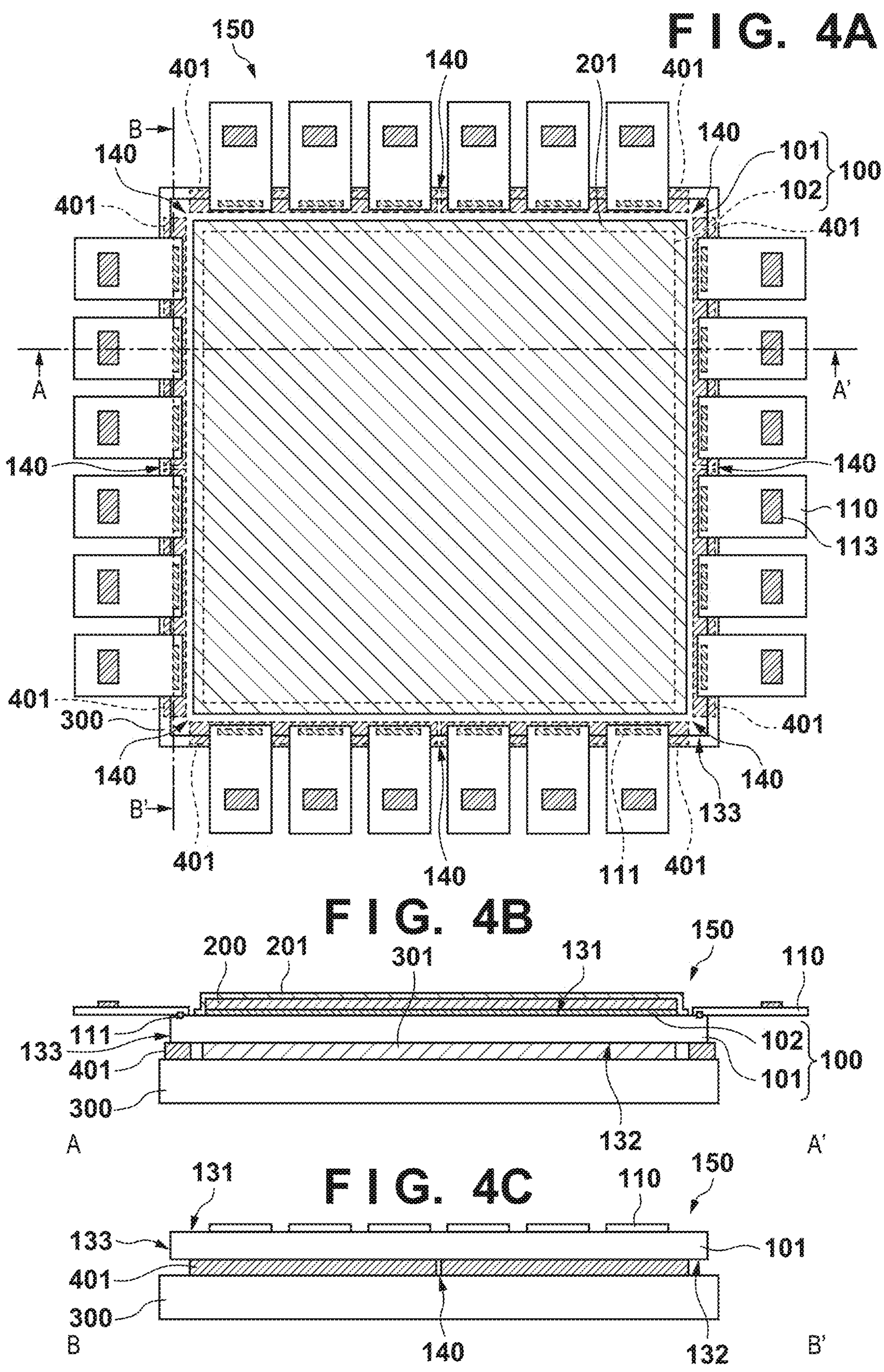
FIGS. 4A to 4C are views showing an example of the arrangement of the radiation imaging apparatus according to this embodiment.
Figures 5A, 5B, 5C:
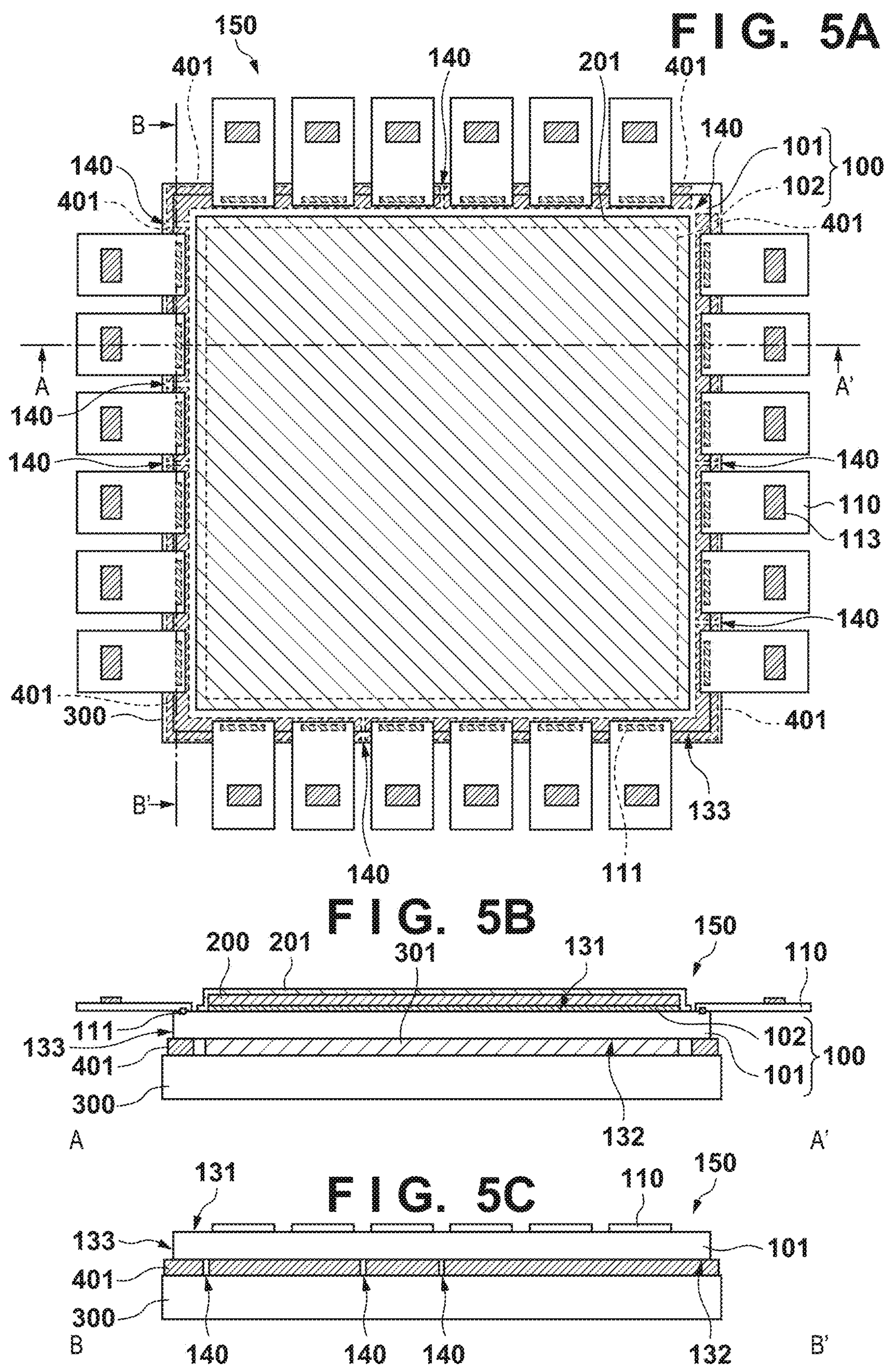
FIGS. 5A to 5C are views showing an example of the arrangement of the radiation imaging apparatus according to this embodiment.

In the arrangement shown in FIG. 2A, the support member 401 is separately provided for each of the sides of the rectangular sensor panel 100. However, this is not exhaustive. For example, as shown in FIGS. 4A to 4C, at least two support members 401 may be intermittently provided along one side of the outer edge 133 of the sensor panel 100. In addition, as shown in FIGS. 5A to 5C, the support member 401 may be provided so as to straddle across two sides of the outer edge 133 of the sensor panel 100. Alternatively, one support member 401 may be provided so as to support one electrical connection portion 111 or to support two or more electrical connection portions 111. The passage 140 may be provided at any position. The passage 140 extending from the support member 301 to the outer edge 133 of the sensor panel 100 may be provided between the surface 132 of the sensor panel 100 and the support base 300 without providing any support member 401.

Figures 6A, 6B, 6C:
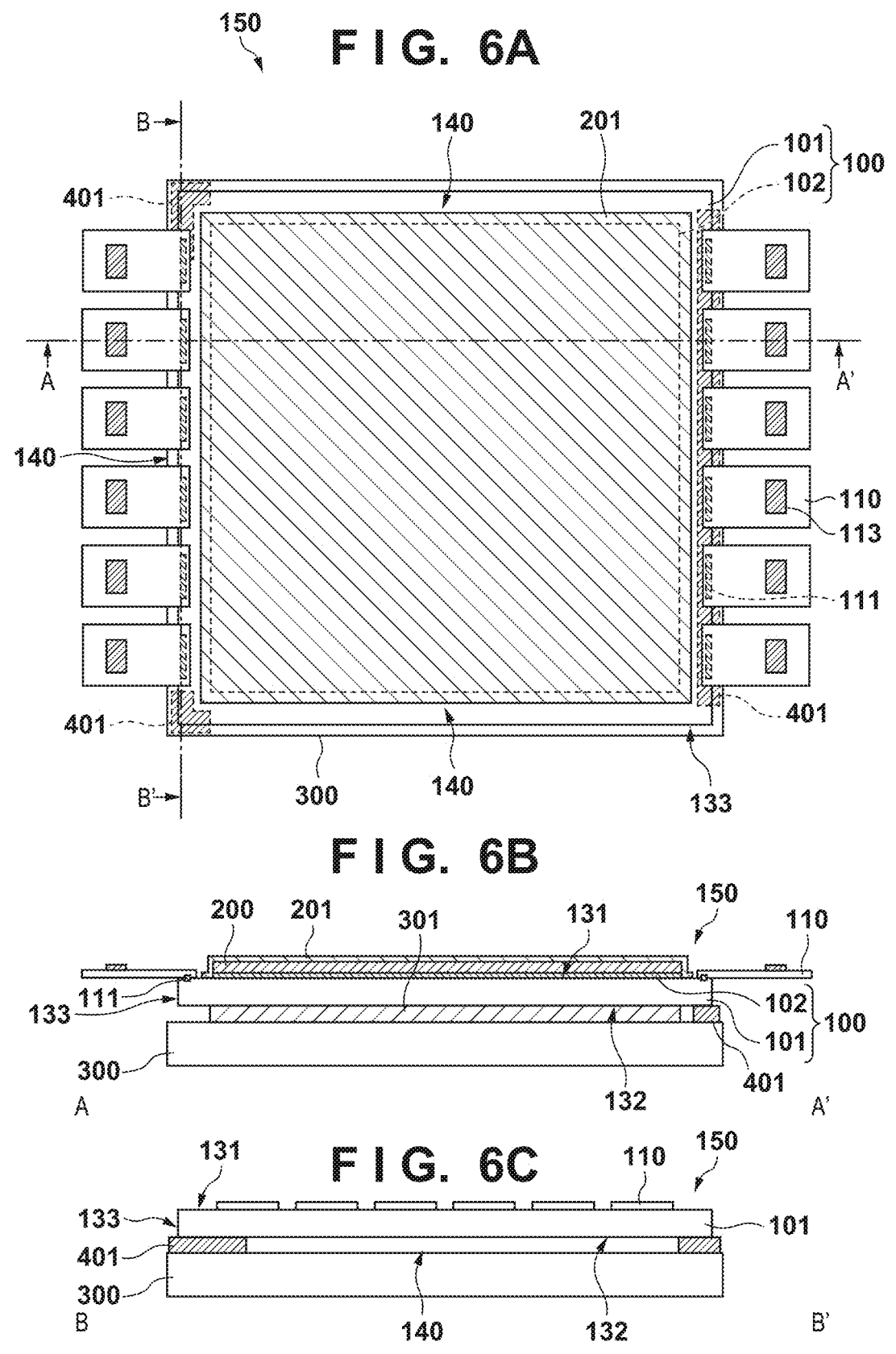

As shown in FIGS. 6A to 6C, the support member 401 need not be provided so as to overlap all the electrical connection portions 111. Although described in detail later, the support member 401 may be provided so as to overlap at least one electrical connection portion 111. In other words, in an orthogonal projection to the surface 131 of the sensor panel 100, the plurality of electrical connection portions 111 may include the electrical connection portion 111 provided at a position where it does not overlap the support member 401. In addition, the electrical connection portions 111 need not be provided along all the sides of the outer edge 133 of the sensor panel 100. The electrical connection portions 111 may be provided along only two sides as shown in FIG. 6A or may be provided along one side or three sides in accordance with the design of the sensor panel 100.

The elastic modulus of the support member 401 may be equal to or higher than that of the support member 301. Providing the support member 401 can improve the impact resistance near the outer edge 133 of the sensor panel 100 which is not provided with the support member 301 and suppress damage and failure of the sensor panel 100. For example, a material for the support member 401 may be selected such that when a pressure of 0.5 MPa (megapascals) is applied to the electrical connection portion 111 supported by the support member 401 in a direction from the surface 131 of the sensor panel 100 to the surface 132, the displacement amount of the outer edge of the sensor panel 100 becomes equal to or less than the thickness of the sensor panel 100 (the substrate 101). Alternatively, for example, a material for the support member 401 may be selected such that when a pressure of 0.5 MPa is applied to the electrical connection portion 111 supported by the support member 401 in the direction from the surface 131 of the sensor panel 100 to the surface 132, the displacement amount of the outer edge of the sensor panel 100 becomes equal to or less than 100 μm (micrometers). This makes it possible to suppress damage to the sensor panel 100 when, for example, the wiring member 110 is connected to the electrical connection portion 111 by pressure-bonding.

An example of a manufacturing method for the radiation imaging apparatus 150 will be described next. First of all, as shown in FIGS. 7A to 7C, the sensor panel 100 is prepared. The sensor panel 100 includes the surface 131 provided with the pixel array 102 and the electrical connection portions 111 and the surface 132 on the opposite side to the surface 131. In this step, various types of existing techniques can be used.

For example, the pixel array 102 and the electrical connection portions 111 are formed on the substrate 101 such as a glass substrate by using various types of semiconductor processes. Subsequently, the scintillator 200 is formed so as to cover the pixel array 102. The scintillator 200 is formed by simultaneously heating and depositing CsI and TlI in a vacuum chamber. When a powder phosphor is used as the scintillator 200, the scintillator 200 is formed by, for example, applying and drying GOS or the like.

The scintillator protective layer 201 is formed so as to cover the scintillator 200. For example, the scintillator protective layer 201 is formed by bonding an aluminum sheet coated with an adhesive compound to the scintillator 200 so as to cover it by using a roll laminator. As the scintillator protective layer 201, a polyparaxylene layer or the like may be formed by using a chemical vapor deposition (CVD) method. In this case, for example, the sensor panel 100 on which the scintillator 200 is formed is installed in a CVD chamber, and a polyparaxylene film is formed while the stage on which the sensor panel 100 is installed is rotated at 5 rpm after the chamber is vacuumed to about 30 Pa.

Figures 8, 9:
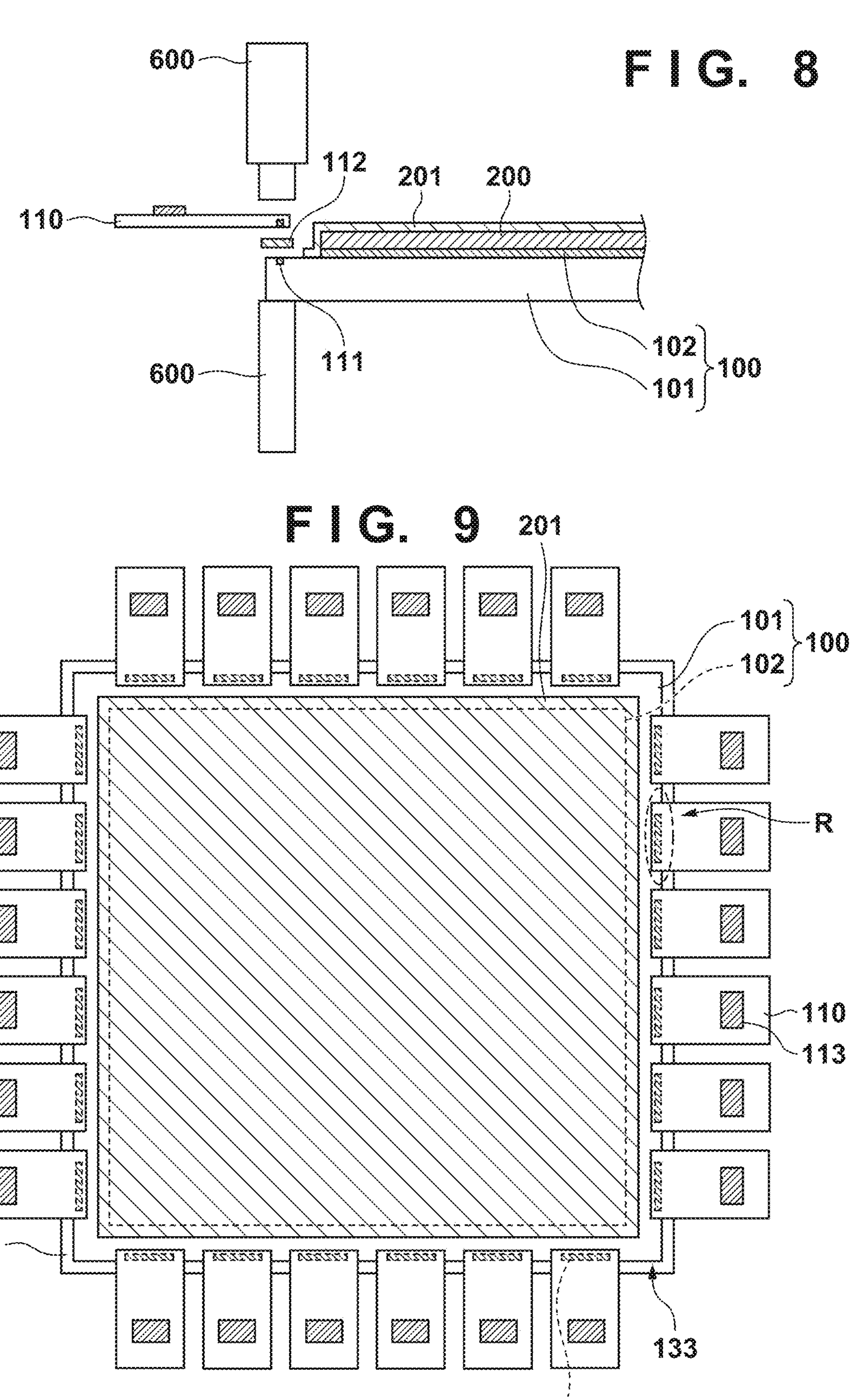
FIG. 8 is a view showing an example of the manufacturing method for the radiation imaging apparatus according to this embodiment.
FIG. 9 is a view showing an example of the manufacturing method for the radiation imaging apparatus according to this embodiment.
Figures 10A, 10B:
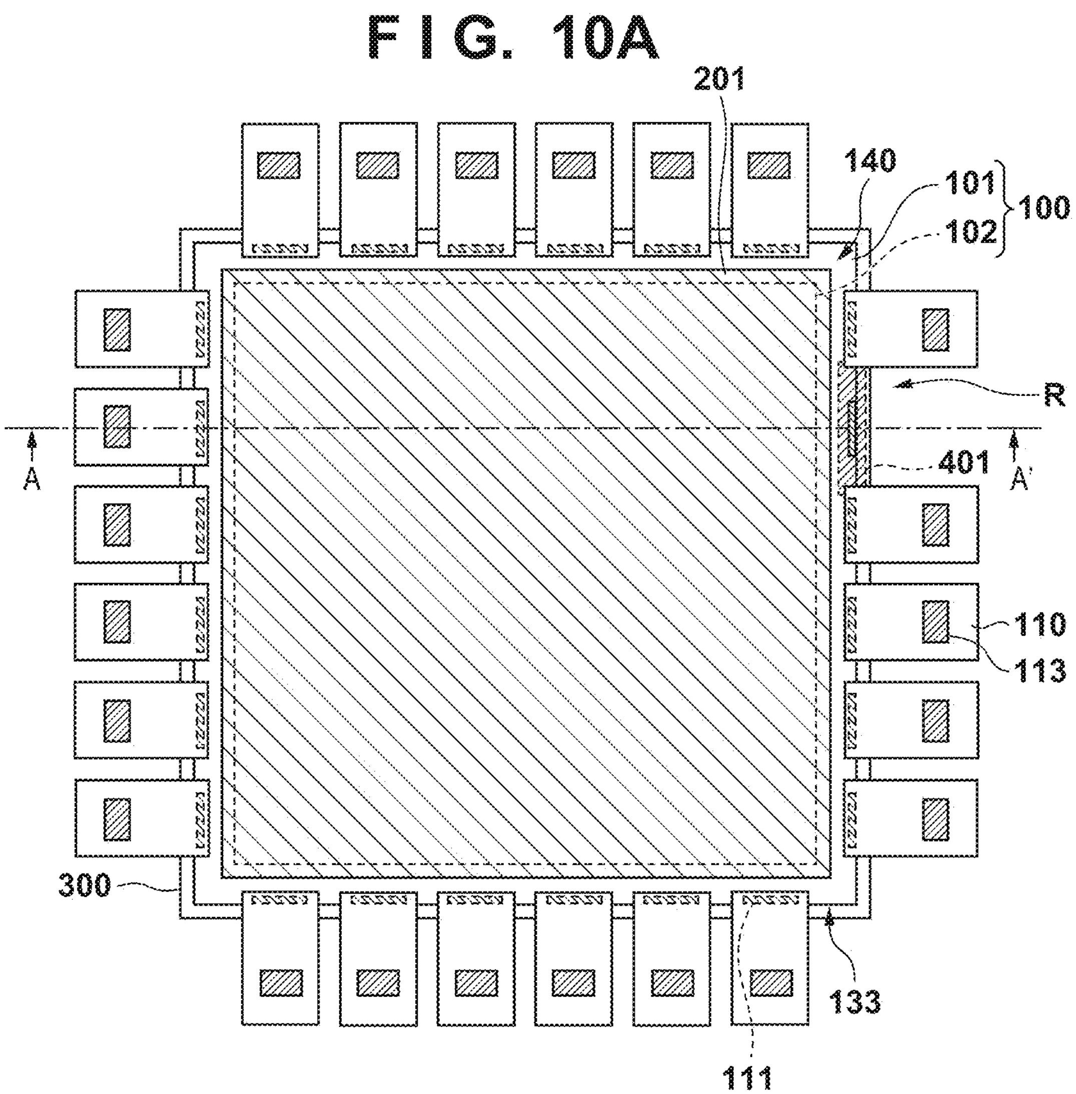
FIGS. 10A and 10B are views showing an example of the manufacturing method for the radiation imaging apparatus according to this embodiment.

After the formation of the scintillator 200 and the scintillator protective layer 201, the wiring members 110 are connected to the electrical connection portions 111. For example, as shown in FIG. 8, the wiring member 110 is connected, through the joining member 112 such as an anisotropic conductive film (ACF) or a gold bump, to the electrical connection portion 111 provided on the surface 131 of the sensor panel 100. For example, the wiring member 110 is connected to the electrical connection portion 111 by thermal pressure-bonding for 5 sec to 5 min by using a pressure-bonding apparatus 600 under the conditions of a temperature of 100° C. to 200° C. (Celsius) and a pressure of 0.5 MPa to 5 MPa. The wiring member 110 may be connected to the electrical connection portion 111 by a method without heating and pressurization without using pressure-bonding. The wiring member 110 may be connected to the electrical connection portion 111 before the formation of the scintillator 200 and the scintillator protective layer 201.

The next step includes fixing the sensor panel 100 to the support base 300 that supports the surface 132 of the sensor panel 100 through the support member 301 and the support member 401. The support member 301 may be, for example, a silicone-based adhesive compound having a thickness of 100 μm. The support member 301 is provided in contact with a region overlapping a portion of the surface 132 of the sensor panel 100 on which the pixel array 102 is provided.

When the sensor panel 100 is fixed to the support base 300 through the support member 301, the support member 401 may be provided between the support base 300 and the surface 132 of the sensor panel 100. Alternatively, after the sensor panel 100 is fixed to the support base 300 through the support member 301, the support member 401 may be formed. As described above, the support member 401 is provided at a position where it overlaps the electrical connection portions 111. The support member 401 may be only coated with a two-component epoxy resin whose hardening is promoted by mixing two types of liquids. Alternatively, a plate material may be arranged on the support base 300, and an epoxy resin is applied onto the plate material.

The radiation imaging apparatus 150 is manufactured by using the above steps. Providing the support member 401 will increase the rigidity near the outer edge 133 of the sensor panel 100. This can suppress damage to the sensor panel 100 even if an impact is applied to the radiation imaging apparatus 150 while, for example, it is moved or used. As a result, the reliability of the radiation imaging apparatus 150 improves. In addition, as shown in FIG. 6A, the support member 401 is provided near even the electrical connection portions 111 immediately below which the support member 401 is not provided. Accordingly, it is possible to suppress damage to the sensor panel 100 as compared with the case where the support member 401 is not provided.

As described above, the passage 140 extending from the support member 301 to the outer edge 133 of the sensor panel 100 is provided between the surface 132 of the sensor panel 100 and the support base 300, and the support member 401 does not continuously surround the pixel array 102. This can suppress the distortion of the sensor panel 100 due to, for example, a change in environmental temperature and suppress the occurrence of an artifact. That is, it is possible to suppress a deterioration in the image quality of an image obtained by the radiation imaging apparatus 150.

According to the manufacturing method described above, when the sensor panel 100 is fixed to the support base 300, the support member 301 and the support member 401 are provided at similar timings. However, the manufacturing method is not limited to this. An example of a manufacturing method for the radiation imaging apparatus 150 which is different from the above manufacturing method will be described below.

Steps before the step of fixing the sensor panel 100 to the support base 300 may be similar to those in the manufacturing method described above. In this case, the sensor panel 100 with the wiring members 110 connected to the electrical connection portions 111 is prepared. Next, the sensor panel 100 is fixed to the support base 300 that supports the surface 132 of the sensor panel 100 through the support member 301. At this time, the support member 401 is not provided yet.

Subsequently, the radiation imaging apparatus 150 is manufactured by using proper steps, and the completion inspection of the radiation imaging apparatus 150 is conducted. In this inspection, for example, a fault in connection through the wiring member 110 or a fault in the circuit 113 provided on the wiring member 110 is sometimes found. Assume that a fault is found in the wiring member 110 connected to the electrical connection portion 111 provided at a position R indicated in FIG. 9. In this case, it is useful from the viewpoint of cost to replace only the wiring member 110 in which a fault is found. Accordingly, based on the result obtained in the inspecting step, the wiring member 110 provided at the position R is detached from the electrical connection portion 111. Subsequently, the joining member 112 left on the surface 131 of the sensor panel 100 is removed by using, for example, a solvent such as acetone or methyl ethyl ketone (MEK).

Next, the wiring member 110 different from the detached wiring member 110 is connected to the electrical connection portion 111 provided at the position R. In this case, a space formed between the electrical connection portion 111 provided at the position R and the support base 300 due to the support member 301 provided so as to overlap the pixel array 102. Accordingly, when the wiring member 110 is connected to the electrical connection portion 111 provided at the position R, the pressure generated when the wiring member 110 is subjected to pressure-bonding may damage a portion of the sensor panel 100 which is located near the position R.

Before the wiring member 110 is connected to the electrical connection portion 111, as shown in FIG. 10, the support member 401 is arranged in a region overlapping at least the electrical connection portion 111 provided at the position R in an orthogonal projection to the surface 131 of the sensor panel 100. The support member 401 may be formed by being coated with an epoxy resin or may be formed by arranging a plate material on the support base 300 and applying an epoxy resin onto the plate material.

After the formation of the support member 401, the new wiring member 110 is connected to the electrical connection portion 111. A step of connecting the wiring member 110 is similar to the step described with reference to FIG. 8. When the wiring member 110 is connected, the support member 401 is provided between the sensor panel 100 and the support base 300. This makes it possible to ensure the rigidity of the sensor panel 100 (the substrate 101) at the position R and suppress a fault in the connection between the electrical connection portion 111 and the new wiring member 110 and damage to the sensor panel 100. As a result, it is possible to improve the reliability of the radiation imaging apparatus 150 and enhance the yield. In addition, as described above, the passage 140 is provided between the surface 132 of the sensor panel 100 and the support base 300, and the support member 401 does not continuously surround the pixel array 102. This makes it possible to suppress the distortion of the sensor panel 100 due to a change in environmental temperature and suppress the occurrence of an artifact. While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from Japanese Patent Application No. 2023-097243, filed Jun. 13, 2023, which is hereby incorporated by reference herein in its entirety.

What is claimed is:

1. A radiation imaging apparatus comprising:

a sensor panel including a first surface provided with a pixel array and a plurality of electrical connection portions and a second surface on an opposite side to the first surface;

a plurality of wiring members connected to the plurality of electrical connection portions, respectively; and a support base configured to support the second surface through a first support member and a plurality of second support members, wherein in an orthogonal projection to the first surface, the first support member is provided so as to overlap the pixel array, the plurality of electrical connection portions is provided between a region within which the first support member overlaps the pixel array and an outer edge of the sensor panel, the plurality of second support members include one second support member provided so as to overlap and configured to support not less than two of the plurality of electrical connection portions, and the plurality of electrical connection portions include an electrical connection portion provided at a position where the electrical connection portion does not overlap the plurality of second support members, each of the plurality of second support members is fixed to at least one of the second surface, and the support base, and a passage extending from the first support member to the outer edge is provided between the second surface and the support base so as not to overlap the plurality of second support members in an orthogonal projection to the first surface.

2. The apparatus according to claim 1, wherein in a case where a pressure of 0.5 MPa (megapascals) is applied to one of the plurality of electrical connection portions in a direction from the first surface to the second surface, a displacement amount of the outer edge is not more than a thickness of the sensor panel.

3. The apparatus according to claim 1, wherein in a case where a pressure of 0.5 MPa (megapascals) is applied to one of the plurality of electrical connection portions in a direction from the first surface to the second surface, a displacement amount of the outer edge is not more than 100 μm (micrometers).

4. The apparatus according to claim 1, wherein an elastic modulus of the plurality of second support members is not less than an elastic modulus of the first support member.

5. The apparatus according to claim 1, wherein at least two of second support members of the plurality of second support members are intermittently provided along one side of the outer edge.

6. The apparatus according to claim 1, wherein in an orthogonal projection to the first surface, the plurality of second support members are intermittently provided so as to surround the pixel array.

7. The apparatus according to claim 1, wherein the plurality of wiring members include a wiring member provided with a circuit configured to operate the pixel array.

8. The apparatus according to claim 1, wherein a scintillator is provided so as to cover the first surface.

9. A radiation imaging system comprising:

the radiation imaging apparatus according to claim 1; and a processing apparatus configured to process a signal output from the radiation imaging apparatus.

10. A manufacturing method for a radiation imaging apparatus, the method comprising:

preparing a sensor panel including a first surface provided with a pixel array and a plurality of electrical connection portions and a second surface on an opposite side to the first surface; and fixing the sensor panel to a support base supporting the second surface through a first support member, wherein in an orthogonal projection to the first surface, the first support member is provided so as to overlap the pixel array, and the plurality of electrical connection portions is provided between a region in which the first support member overlaps the pixel array and an outer edge of the sensor panel, the method further comprises providing a plurality of second support members including one second support member provided so as to overlap and configured to support not less than two of the plurality of electrical connection portions, and connecting a plurality of wiring members to the plurality of electrical connection portions, in an orthogonal projection to the first surface, the plurality of electrical connection portions include an electrical connection portion provided at a position where the electrical connection portion does not overlap the plurality of second support members, each of the plurality of second support members is fixed to at least one of the second surface, and the support base, and a passage extending from the first support member to the outer edge is provided between the second surface and the support base so as not to overlap the plurality of second support members in an orthogonal projection to the first surface.

11. The method according to claim 10, wherein the connecting is performed after the providing, in the preparing, a wiring member different from the plurality of wiring members is connected to one of the electrical connection portions, and the method further comprises detaching the different wiring member from the one of the plurality of electrical connection portions between the fixing and the providing.

12. The method according to claim 11, further comprising inspecting the radiation imaging apparatus between the fixing and the detaching, wherein the different wiring member is detached based on a result of the inspecting.

* * * * *